United States Patent [19]

Kohl

[11] 4,382,062

[45] May 3, 1983

[54] TEST AGENT FOR THE DETECTION OF COUPLING COMPOUNDS, AND A PROCESS FOR ITS PREPARATION

[75] Inventor: Helmut Kohl, Wetter, Fed. Rep. of Germany

[73] Assignee: Behringwerke Aktiengesellschaft, Marburg, Fed. Rep. of Germany

[21] Appl. No.: 270,375

[22] Filed: Jun. 4, 1981

[30] Foreign Application Priority Data

Jun. 6, 1980 [DE] Fed. Rep. of Germany ....... 3021305

[51] Int. Cl.³ .................... G01N 33/52; G01N 33/72
[52] U.S. Cl. .......................................... 422/56; 427/2; 436/97; 436/903
[58] Field of Search ................. 23/230 B, 929, 905; 422/56; 252/408; 436/903, 97; 427/2

[56] References Cited

U.S. PATENT DOCUMENTS

| | | | |
|---|---|---|---|
| 3,850,576 | 11/1974 | Rittersdorf et al. | 23/929 X |
| 3,853,476 | 12/1974 | Rittersdorf et al. | 23/230 B X |
| 4,161,507 | 7/1979 | Hirsch | 23/929 X |
| 4,246,133 | 1/1981 | Gindler | 23/230 B X |
| 4,290,771 | 9/1981 | Hirsch | 23/929 X |

OTHER PUBLICATIONS

Hendrickson et al., "Organic Chemistry-Third Edition", McGraw-Hill Book Co., 1970, pp. 800-801.

*Primary Examiner*—Arnold Turk
*Attorney, Agent, or Firm*—Curtis, Morris & Safford

[57] ABSTRACT

A test agent for the detection of coupling compounds in liquids is described, which essentially consists of an adsorbent matrix containing a diazonium salt as the reagent and a phosphonium salt to stabilize said test agent. Furthermore there is described a process for the preparation of said test agent.

7 Claims, No Drawings

TEST AGENT FOR THE DETECTION OF COUPLING COMPOUNDS, AND A PROCESS FOR ITS PREPARATION

The invention relates to a test agent for the detection of coupling compounds in liquids, which essentially consists of an adsorbent matrix containing a diazonium salt as the reagent and a phosphonium salt.

The analytical determination of coupling compounds, such as, for example, bilirubin or urobilinogen, in body fluids using diazonium salts is a familiar method. Examples of this determination are given, for example, in German Offenlegungsschrift No. 2,623,087 and in German Patent Specification No. 2,936,745.

In cases of liver damage and biliary blockages, bilirubin already appears prematurely in the urine. It can be determined therein by means of a coupling reaction with a diazonium salt. Sensitive colors which are relatively difficult to recognize are produced in these detection reactions.

It is at present customary to carry out rapid orientating determinations of bilirubin in the serum or urine using rapid tests. These rapid tests are test agents comprising a sheet-like carrier matrix which has been impregnated with diazonium salts and other auxiliaries. Different rapid tests are now in general combined in combination tests. A combination test strip can contain, for example, test areas for detecting glucose, bilirubin, protein and ketones. Combination test strips of this type are marketed, inter alia, under the trade mark RAPIGNOST®.

In general, the rapid test strips are extremely unstable; thus, the reagents already decompose as a result of atmospheric moisture. In combination test strips, it is also possible that adjacent test areas have an adverse effect on one another. It has thus been found that a bilirubin test paper containing, inter alia, a dichlorobenzenediazonium salt discolors very easily if it is exposed to an atmospheric humidity of >60% at room temperature or if it is processed together with test areas which have been buffered strongly basic. In each case yellow-colored or red-colored bilirubin test areas are then formed. These discolorations can, however, also occur during storage of the rapid diagnostics. A decisive factor in their diagnostic effectiveness is that the colorless papers do not discolor, since only then can the weak color reactions which occur in the case of a positive bilirubin reaction be detected.

The diazonium salts customarily used are extremely unstable compounds. They are marketed in the stabilized form. Stabilizers can be, inter alia: sulfonic acids or Lewis acids, such as, for example, $AlCl_3$, $SnCl_2$ or $BF_4^-$.

German Offenlegungsschrift No. 2,007,013 claims sulfonic acids as stabilizers for diazonium salts on test strips. The additives serve to maintain a given content of diazonium salt on the test strip. The use of Lewis acids is described in German Offenlegungsschrift No. 2,012,558. These compounds are said to have a color-intensifying effect.

The use of phosphoric acid diesters is claimed in German Auslegeschrift No. 2,240,357. These compounds have been found to have an activating effect on the determination of bilirubin. No stabilizing actions are mentioned.

The diazonium salt used is stabilized with $NaHSO_4$ and additionally also contains a $BF_4^-$ anion. A test paper can in this way be stored for several years without resulting losses in quality. Nevertheless, if the bilirubin test paper, for production reasons, is processed together with other test papers, in particular with ketone test paper, it very rapidly becomes pink-colored in spite of stringent precautionary measures.

The aim of the present invention was thus a stabilizer for rapid diagnostics for the detection of coupling compounds in body fluids. The stabilizer should protect the rapid diagnostics from discoloration which could occur during their preparation or storage.

The objective is achieved by using a phosphonium salt as a stabilizer for rapid diagnostics for the detection of coupling compounds in body fluids.

The invention relates to a test agent for the detection of coupling compounds in body fluids, consisting essentially of an adsorbent matrix, which is impregnated with a diazonium salt and, if appropriate, a stabilizer for this salt, which test agent contains a phosphonium salt.

Furthermore, the invention relates to the use of alkylated and/or arylated phosphonium salts, which can optionally be simultaneously substituted by alkyl and aryl groups. Alkylated phosphonium compounds which are in the form of halides, in particular in the form of bromides, are preferred, and tetraalkylphosphonium salts of this type are particularly preferred. Ethyltrioctylphosphonium bromide is especially preferred.

Further suitable stabilizers are, for example, tetrabutylphosphonium bromide, hexadecyltributylphosphonium bromide and phenyltributylphosphonium bromide.

However, the choice of anion is not critical and any desired anions, such as, for example, halide, hydroxide, sulfate or sulfonate, can be used.

The stabilizers according to the invention can be prepared according to "Methoden der Organischen Chemie" ("Methods of Organic Chemistry"), Houben-Weyl, Volume XII, 1, page 79 et seq.

The test agent according to the invention consists of an adsorbent carrier matrix in which the reagent for the detection of compounds which couple with the diazonium salt, and a phosphonium salt are embedded. All absorbent sheet-like structures of natural or synthetic origin, such as, for example, fleeces, paper, asbestos or polymer films, can be used as the carrier matrix.

The test agent can be prepared in different ways. Thus, the phosphonium salts can be applied to the test paper before or after the particular diazonium salt. They can also be applied to the rapid diagnostic together with the diazonium salt. A process in which an indicator base-paper is first impregnated with a diazonium salt and other auxiliaries, such as, for example, buffer salts, stabilizers and wetting agents in water or water-miscible organic solvents, and the phosphonium salt, in an organic solvent, such as alcohol (for example n-propanol) or polar aprotic solvents (for example ethylene glycol), is then applied in a second step has proved suitable. When choosing the solvent for the second impregnation, it should be ensured that this no longer detaches the components applied during the first impregnation from the carrier matrix.

The preferred process for the preparation of the present test agent thus comprises several stages, the first of which is impregnation of the adsorbent matrix in the discussed manner. After drying, the carrier can be laminated onto paper or a film of plastic.

The amount of the particular stabilizer is not critical and is only limited by the solubility of the stabilizer in the chosen solvent. The particular concentration of the stabilizer can thus be, for example, between 0.1% and 10%, but concentrations between 0.4% and 5% are preferred.

When the phosphonium compounds are used, no intolerable discoloration of the bilirubin papers occurs. No stabilizing effects of the phosphonium salts on the diazonium salt content have been observed. Furthermore, the test papers are thus also sufficiently stable. They do not activate the detection of bilirubin.

When the present test agent is used, it is immersed for a brief period in the liquid to be investigated and is taken out immediately. A specific coloration develops, which depends on the content of coupling compounds in the liquid.

The unexpectedly great advantage of the invention is exhibited, surprisingly, in comparison investigations with rapid diagnostics according to the state of the art.

For a comparison experiment, two test papers were prepared. The test paper was impregnated, according to Example 1, with a diazonium salt in solution 1. To prepare test paper 2, test paper 1 was subsequently also treated with a solution of 10 g/l of ethyltrioctylphosphonium bromide in n-propanol (solution 2). After drying, both papers were colorless.

In the first experiment, test papers 1 and 2 were kept in a climatically controlled chamber at 25° C. and at a relative atmospheric humidity of 70% for twelve hours. Test paper 1 was then yellow-colored and the color of test paper 2 had not changed. In a further experiment, the test papers 1 and 2 were welded onto a plastic carrier together with test papers which had been buffered to be strongly basic, for the determination of ketone bodies. This carrier was cut into test strips, which were kept at a relative atmospheric humidity of 70% or 10% and at 50° C. Under all the storage conditions, the test papers 1 became pink-colored and the test papers 2 remained colorless. The test papers 1 were no longer suitable for the determination of bilirubin, and it was still possible clearly to detect traces of bilirubin in the region of about 0.4 mg% with the test papers 2.

The invention is illustrated in more detail by the following example:

EXAMPLE

Solution 1: 0.7 g of pyrazole-3-diazonium tetrafluoroborate, 40 g of m-phosphoric acid, 20 g of sodium bisulfate and 5 g of dodecylbenzene-sulfonate are dissolved in 300 ml of water.

Solution 2: 1 g of ethyl-trioctylphosphonium bromide is dissolved in 100 ml of n-propanol.

Schleicher and Schüll 2316 paper is impregnated with solution 1 and dried (test paper 1).

The dry test paper 1 is treated with solution 2 (test paper 2). Both papers exhibit the effects described.

However, it is also possible to treat an indicator base-paper first with solution 2 and then with solution 1. This test paper does not differ from the test paper 2 mentioned above.

I claim:

1. A stabilized rapid diagnostic agent for the detection of coupling compounds in biologic fluids consisting essentially of an adsorbent carrier matrix comprising fleeces, paper, asbestos or polymer films, said matrix being impregnated with a diazonium salt as reagent for said coupling compounds and a phosphonium salt as stabilizer for said rapid diagnostic agent wherein said phosphonium salt is present in an effective amount to stabilize said rapid diagnostic agent.

2. The stabilized rapid diagnostic agent of claim 1 further containing an effective stabilizer for said diazonium salt.

3. The stabilized rapid diagnostic agent of claim 1 wherein said phosphonium salt contains an alkyl or aryl group, or both.

4. The stabilized rapid diagnostic agent of claim 1 wherein said phosphonium salt is ethyl-trioctylphosphonium bromide.

5. A process for the preparation of a stabilized rapid diagnostic agent for the detection of coupling compounds in biologic fluids which consists essentially of impregnating an adsorbent carrier matrix comprising fleeces, paper, asbestos or polymer films with a diazonium salt as reagent for said coupling compounds and thereafter impregnating said matrix with an effective amount of a phosphonium salt to stabilize said rapid diagnostic agent.

6. The process of claim 5 wherein an effective stabilizer is added to said diazonium salt to stabilize said diazonium salt.

7. The process of claim 5 wherein said phosphonium salt is ethyl-trioctylphosphonium bromide.

* * * * *